United States Patent
Ewald et al.

(10) Patent No.: US 6,875,243 B2
(45) Date of Patent: Apr. 5, 2005

(54) CATALYSTS FOR PREPARING POLYISOCYANATES CONTAINING ISOCYANURATE GROUPS, AND THEIR USE

(75) Inventors: Michael Ewald, Marl (DE); Manuela Windmueller, Marl (DE); Waltraud Poersch, Herne (DE); Stephan Kohlstruk, Duelmen (DE)

(73) Assignee: Degussa AG, Duesseldorf (DE)

( * ) Notice: Subject to any disclaimer, the term of this patent is extended or adjusted under 35 U.S.C. 154(b) by 155 days.

(21) Appl. No.: 10/304,945

(22) Filed: Nov. 27, 2002

(65) Prior Publication Data

US 2003/0109665 A1 Jun. 12, 2003

(30) Foreign Application Priority Data

Dec. 7, 2001 (DE) .......................... 101 60 305

(51) Int. Cl.⁷ ..................... D06M 15/564; B01J 31/22; C07D 251/34; C08G 18/79; C09D 175/04
(52) U.S. Cl. ................... 8/115.6; 8/190; 428/423.1; 428/423.4; 428/425.1; 502/158; 502/162; 502/164; 528/51; 528/52; 528/53; 528/73; 544/193; 544/222; 556/410; 556/411
(58) Field of Search ............... 8/115.6, 190; 428/423.1, 428/423.4, 425.1; 502/158, 162, 164; 528/51, 52, 53, 73; 544/193, 222; 556/410, 411

(56) References Cited

U.S. PATENT DOCUMENTS

| | | | |
|---|---|---|---|
| 4,324,879 A | 4/1982 | Bock et al. ............... 528/45 |
| 4,412,073 A | 10/1983 | Robin ..................... 544/193 |
| 4,537,961 A | 8/1985 | Robin ..................... 544/193 |
| 4,675,401 A | 6/1987 | Robin ..................... 544/193 |
| 4,697,014 A | 9/1987 | Robin ..................... 544/193 |
| 4,771,117 A | 9/1988 | Citron et al. ............ 526/194 |
| 4,960,848 A | * 10/1990 | Scholl et al. ............ 528/48 |
| 5,013,838 A | * 5/1991 | Scholl .................... 544/193 |
| 5,556,935 A | * 9/1996 | Traubel et al. ........... 528/99 |
| 5,798,431 A | 8/1998 | Brahm et al. ............. 528/73 |
| 5,914,383 A | * 6/1999 | Richter et al. ........... 528/59 |
| 6,090,939 A | * 7/2000 | Richter et al. ........... 544/67 |
| 6,452,003 B1 | 9/2002 | Ewald et al. ............. 544/222 |
| 6,552,154 B1 | 4/2003 | Kohlstruk et al. ........ 528/52 |
| 6,703,471 B2 | * 3/2004 | Kohlstruk et al. ........ 528/54 |

FOREIGN PATENT DOCUMENTS

| | | |
|---|---|---|
| EP | 0 057 653 | 8/1982 |
| EP | 0 339 396 | 11/1989 |
| EP | 0 379 914 | 8/1990 |
| EP | 0 413 465 | 2/1991 |
| EP | 0 571 867 | 12/1993 |
| EP | 0 798 299 | 10/1997 |
| EP | 0 896 009 | 2/1999 |
| EP | 0 962 454 | 12/1999 |

* cited by examiner

*Primary Examiner*—Rabon Sergent
(74) *Attorney, Agent, or Firm*—Oblon, Spivak, McClelland, Maier & Neustadt, P.C.

(57) ABSTRACT

Catalysts and processes for preparing polyisocyanates containing isocyanurate groups, and their use, wherein the catalysts are represented by the following formula (1):

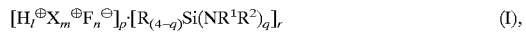

wherein
  $n = m + l$ with $1 \geq m/n > 0$, and $l \geq 0$,
  $p > 0$ and $r > 0$, and the ratio $p/r$ is any value,
  $q = 1$ or $2$, and
  $R$, $R^1$, $R^2$ and $X$ are as defined.

48 Claims, No Drawings

CATALYSTS FOR PREPARING POLYISOCYANATES CONTAINING ISOCYANURATE GROUPS, AND THEIR USE

BACKGROUND OF THE INVENTION

1. Field of the Invention

The present invention relates to catalysts and a process for preparing polyisocyanates containing isocyanurate groups, to polyisocyanates thus prepared, and to their use.

2. Description of the Background

For high-grade one- and two-component polyurethane coating materials featuring high light stability and weathering stability, the isocyanate component used comprises, in particular, polyisocyanate mixtures containing isocyanurate and uretdione groups. The oligomerization or polymerization of isocyanates to give such polyisocyanates has been known for a long time. A range of preparation processes have been developed, differing from one another in catalyst selection, in the organic isocyanates used, or in technical parameters of the process (cf. e.g. GB Patent 1391066, EP 82 987, DE 39 02 078, EP 339 396, EP 224 165; see also H. J. Laas et al. in *J. Prakt. Chem.* 336 (1994), 185 ff.).

Isocyanates suitable for trimerization, examples being aromatic, cycloaliphatic, and aliphatic diisocyanates and higher polyisocyanates, can be prepared by a variety of methods (Annalen der Chemie 562 (1949), 75 ff.). Processes established in the industry include in particular preparation by phosgenating organic polyamines to the corresponding polycarbamoyl chlorides and the thermal cleavage of these chlorides into organic polyisocyanates and hydrogen chloride. Alternatively, organic polyisocyanates can be prepared without the use of phosgene, i.e., by phosgene-free processes. According to EP 126 299, EP 126 300 and EP 355 443, for example, (cyclo)aliphatic diisocyanates—such as 1,6-hexamethylene diisocyanate (HDI) and/or isomeric aliphatic diisocyanates having 6 carbon atoms in the alkylene radical, and 1-isocyanato-3-iso-cyanatomethyl-3,5,5-trimethylcyclohexane (isophorone diisocyanate or IPDI)—can be prepared by reaction of the parent (cyclo)aliphatic diamines with urea and alcohols to give (cyclo)aliphatic biscarbamic esters and the thermal cleavage thereof into the corresponding diisocyanates and alcohols.

For oligomerization, the (cyclo)aliphatic diisocyanates are reacted in the presence of the catalyst, with or without the use of solvents and/or auxiliaries, until the desired degree of conversion has been achieved. One of the terms used in this context is partial trimerization, since the target conversion is generally well below 100%. Afterward, the reaction is terminated by deactivating the catalyst and the excess monomeric diisocyanate is usually separated off, generally by flash or thin-film distillation. Deactivation is carried out thermally or by adding a catalyst inhibitor. Suitable examples include acids such as p-toluenesulfonic acid or bis(2-ethylhexyl)phosphate, alkylating agents or else acylating reagents.

As catalysts for the trimerization of isocyanates to the target polyisocyanates containing isocyanurate and possibly uretdione groups it is possible, for example, to use tertiary amines, phosphines, alkali metal phenoxides, amino silanes, quaternary ammonium hydroxides or quaternary ammonium carbonates. Highly suitable oligomerization catalysts also include hydroxides, halides or carboxylates of hydroxyalkylammonium ions (cf., e.g., EP 351 873, EP 798 299, U.S. Pat. No. 5,290,902), alkali metal salts, and tin salts, zinc salts, and lead salts of alkylcarboxylic acids. Depending on the catalysts, the use of various cocatalysts such as OH-functionalized compounds or Mannich bases composed of secondary amines and aldehydes or ketones, for example, is also possible.

Depending on the type of catalyst used and the reaction temperature, polyisocyanates are obtained with different proportions of isocyanurate and/or uretdione groups. The products are usually clear but may also have a greater or lesser yellow coloration depending on catalyst type, diisocyanate quality, reaction temperature and reaction regime. For the preparation of high-grade polyurethane coating materials, however, products whose color number is as low as possible are desired.

An appropriate catalyst may be selected according to different criteria. Of particular advantage with a view to the trimerization of isocyanates on an industrial scale, for example, is the use of quaternary hydroxylalkylammonium carboxylates as oligomerization catalysts. These choline-type catalysts are thermally labile. It is unnecessary to stop the trimerization on reaching the desired conversion by adding potentially quality-lowering catalyst inhibitors. Instead, targeted thermal deactivation allows optimum process control. The thermal lability also affords advantages from the standpoint of process safety. There is no possibility of uncontrolled reaction "runaway" provided the amount of catalyst added does not exceed the customary level by a multiple.

Aminosilyl compounds have proven advantageous for preparing high color quality polyisocyanates containing isocyanurate groups (U.S. Pat. Nos. 4,412,073, 4,537,961, 4,675,401, 4,697,014). In addition, they permit safe reaction control and can easily be deactivated using water or alcohols.

The class of the aminosilyl catalysts is hampered, however, by the disadvantage of low catalytic activity, so that economic space-time yields can be realized only when relatively large quantities of catalyst are used. This, however, is associated with further disadvantages. On the one hand, it constitutes a serious cost factor, since deactivation irreversibly destroys the catalyst which thus cannot be positively recycled into the process. On the other hand, relatively large amounts of the deactivated catalysts inevitably get into the product, with possibly adverse consequences for its profile of properties.

There is therefore a need for Si-based catalysts for preparing isocyanurate-containing polyisocyanates that do not have the disadvantages of the aminosilyl compounds known in the art.

SUMMARY OF THE INVENTION

It is an object of the present invention, accordingly, to provide novel Si-based catalysts for preparing polyisocyanates containing isocyanurate groups, these catalysts first being distinguished by significantly heightened activity and yet second permitting safe reaction control and process safety.

The invention provides catalysts for the trimerization of isocyanates, of the general formula (I)

$$[H_l^{\oplus} X_m^{\oplus} F_n^{\ominus}]_p \cdot [R_{(4-q)} Si(NR^1 R^2)_q]_r \qquad (I),$$

where
- $n = m+1$ with $1 \geq m/n > 0$, preferably $1 \geq m/n \geq 0.1$, with particular preference $1 \geq m/n \geq 0.25$, and $1 \geq 0$,
- $p > 0$ and $r > 0$ and the ratio $p/r$ can adopt any desired value, preferably between 0.01 and 100, with particular preference between 0.1 and 10, q=1 or 2, R simultaneously or independently of one another stands for a saturated or unsaturated, linear or branched aliphatic or cycloaliphatic radical or aryl, aralkyl, or alkylaryl radical having from 1 to 16 carbon atoms, and two radicals R can be linked with one another via an alkylene bridge, $R^1$ represents R, $SiR_3$ or an amide radical of formula (II)

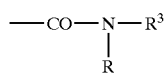  (II), $R^2$ is R or H, it being possible for $R^2$, if $R^1$ is not an amide radical, to be linked to $R^1$ via an alkylene bridge, $R^3$ is R or $SiR_3$, and $X^\ominus$ represents an organic onium cation of the general formula (III)

$R_4^4 E^\oplus$  (III), where

E is nitrogen or phosphorus and $R^4$ represents identical or different, linear or branched aliphatic, cycloaliphatic or araliphatic radicals having from 1 to 20 carbon atoms.

The invention also provides a catalyst for the trimerization of isocyanates, obtained by reacting

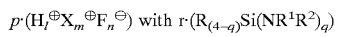

where n=m+1 with $1 \geq m/n > 0$, preferably $1 \geq m/n \geq 0.1$, with particular preference $1 \geq m/n \geq 0.25$, and $1 \geq 0$, p>0 and r>0 and the ratio p/r can adopt any desired value, preferably between 0.01 and 100, with particular preference between 0.1 and 10, q=1 or 2, R represents a saturated or unsaturated, linear or branched aliphatic or cycloaliphatic radical or aryl, aralkyl, or alkylaryl radical having from 1 to 16 carbon atoms, and two radicals R can be linked with one another via an alkylene bridge, $R^1$ represents R, $SiR_3$ or an amide radical of formula (II)

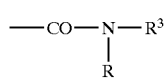  (II), $R^2$ is R or H, it being possible for $R^2$, if $R^1$ is not an amide radical, to be linked to $R^1$ via an alkylene bridge, $R^3$ is R or $SiR_3$, and $X^\ominus$ represents an organic onium cation of the general formula (III)

$R_4^4 E^\oplus$  (III), where

E is nitrogen or phosphorus and $R^4$ represents identical or different, linear or branched aliphatic, cycloaliphatic or araliphatic radicals having from 1 to 20 carbon atoms.

The invention further provides the compounds of the general formula (I)

$[H_l^\oplus X_m^\oplus F_n^\ominus]_{p'}[R_{(4-q)}Si(NR^1R^2)_q]_{r}$  (I), where n=m+1 with $1 \geq m/n > 0$, preferably $1 \geq m/n \geq 0.1$, with particular preference $1 \geq m/n \geq 0.25$, and $1 \geq 0$, p>0 and r>0 and the ratio p/r can adopt any desired value, preferably between 0.01 and 100, with particular preference between 0.1 and 10, q=1 or 2, R simultaneously or independently of one another stands for a saturated or unsaturated, linear or branched aliphatic or cycloaliphatic radical or aryl, aralkyl, or alkylaryl radical having from 1 to 16 carbon atoms, and two radicals R can be linked with one another via an alkylene bridge, $R^1$ represents R, $SiR_3$ or an amide radical of formula (II)

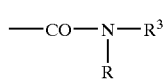  (II), $R^2$ is R or H, it being possible for $R^2$, if $R^1$ is not an amide radical, to be linked to $R^1$ via an alkylene bridge, $R^3$ is R or $SiR_3$, and $X^\ominus$ represents an organic onium cation of the general formula (III)

$R_4^4 E^\oplus$  (III), where

E is nitrogen or phosphorus and $R^4$ represents identical or different, linear or branched aliphatic, cycloaliphatic or araliphatic radicals having from 1 to 20 carbon atoms.

The invention additionally provides a process for preparing a compound of the general formula (I)

$[H_l^\oplus X_m^\oplus F_n^\ominus]_{p'}[R_{(4-q)}Si(NR^1R^2)_q]_{r}$  (I), where n=m+1 with $1 \geq m/n > 0$, preferably $1 \geq m/n \geq 0.1$, with particular preference $1 \geq m/n \geq 0.25$, and $1 \geq 0$.

p>0 and r>0 and the ratio p/r can adopt any desired value, preferably between 0.01 and 100, with particular preference between 0.1 and 10, q=1 or 2, R simultaneously or independently of one another stands for a saturated or unsaturated, linear or branched aliphatic or cycloaliphatic radical or aryl, aralkyl, or alkylaryl radical having from 1 to 16 carbon atoms, and two radicals R can be linked with one another via an alkylene bridge, $R^1$ represents R, $SiR_3$ or an amide radical of formula (II)

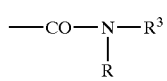  (II), $R^2$ is R or H, it being possible for $R^2$, if $R^1$ is not an amide radical, to be linked to $R^1$ via an alkylene bridge, $R^3$ is R or $SiR_3$, and $X^\ominus$ represents an organic onium cation of the general formula (III)

$R_4^4 E^\oplus$  (III), where

E is nitrogen or phosphorus and

R⁴ represents identical or different, linear or branched aliphatic, cycloaliphatic or aralphatic radicals having from 1 to 20 carbon atoms, in the presence if desired of a solvating agent, at temperatures from −20 to 200° C. In this process a suitable organosilicon compound having at least one Si—N bond is reacted with a suitable fluoride source, in the presence if desired of a solvating agent, at a temperature from −20° C. to 200° C.

Such a process may be accomplished by reacting a fluoride compound represented by the formula:

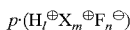

with an organosilicon compound represented by the formula:

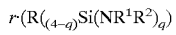

wherein n=m+1 with 1≧m/n>0, and 1≧0, p>0 and r>0, and the ratio p/r is any value, q=1 or 2, R simultaneously or independently of one another represents a saturated or unsaturated, linear or branched aliphatic or cycloaliphatic radical or aryl, aralkyl, or alkylaryl radical having from 1 to 16 carbon atoms, wherein two radicals R may be linked to one another via an alkylene bridge, R¹ represents R, SiR₃ or an amide radical represented by the formula (II):

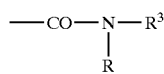

R² is R or H, wherein R², when R¹ is not an amide radical, may be linked to R¹ via an alkylene bridge, R³ is R or SiR₃, and X⊕ represents an organic onium cation represented by the formula (III):

 (III), where

E is nitrogen or phosphorus, and

R⁴ represents identical or different, linear or branched aliphatic, cycloaliphatic or aralphatic radicals having from 1 to 20 carbon atoms.

The present invention also provides a method of trimerizing mono-, di- or polyisocyanates, comprising reacting a mono-, di- or polyisocyanate in the presence of the catalyst described above.

The present invention also provides a process for preparing a polyisocyanate containing isocyanurate groups, comprising trimerizing an organic mono-, di- or polyisocyanate in the presence of the catalyst described above.

The present invention also provides a polyisocyanate containing isocyanurate groups, obtained from the process described above.

The present invention also provides a polyurethane coating, polyurethane dispersion, adhesive, or a 1- and 2-component polyurethane system, comprising the polyisocyanate described above.

In addition, the present invention provides a leather or textile article coated with the polyurethane coating described above.

A more complete appreciation of the invention and many of the attendant advantages thereof will be readily obtained as the same becomes better understood by reference to the following detailed description.

DETAILED DESCRIPTION OF THE INVENTION

The ratio p/r may be any desired value. The range 0.01 to 100 is preferred. This range includes all specific values and subranges therebetween, such as 0.02, 0.05, 0.1, 0.2, 0.5, 1, 2, 5, 10, 25, 50, 75, 90, 95, 98, and 99.

The radical R may have 1 to 16 carbon atoms. This range includes all specific values and subranges therebetween, such as 2, 4, 8, 10, 12, and 14 carbon atoms.

The radical R⁴ may have 1 to 20 carbon atoms. This range includes all specific values and subranges therebetween, such as 2, 4, 8, 10, 12, 14, 16, and 18 carbon atoms.

Organosilicon compounds suitable for preparing the catalysts and compounds of the invention are amino silanes, silyl ureas or silazanes or else mixtures thereof, examples being methylaminotrimethylsilane, dimethylaminotrimethylsilane, dibutylaminotrimethylsilane, diethylaminodimethylphenylsilane, bis(dimethylamino)dimethylsilane, bis(diethylamino)dimethylsilane, bis(dibutylamino)dimethylsilane, bis(dimethylamino)-methylphenylsilane, N-methyl-N-trimethylsilyl-N'-methyl-N'-butylurea, N-trimethylsilyl-N-methyl-N',N'-dimethylurea, N-trimethylsilyl-N-ethyl-N',N'-dimethylurea, N-trimethylsilyl-N-butyl-N'-butyl-N'-trimethylsilylurea, trimethylsilylpyrrolidine, trimethylsilylmorpholine, trimethylsilylpiperidine, trimethylsilylpiperazine, hexamethyldisilazane, heptamethyldisilazane, 1,3-diethyl-1,1,3,3-tetramethyldisilazane, hexaethyldisilazane, and 1,3-diphenyl-1,1,3,3-tetramethyldisilazane.

Fluoride sources suitable for preparing the catalysts and compounds of the invention are quaternary ammonium and phosphonium fluorides, examples being tetrabutyl-, tetraethyl-, tetraoctyl-, tetraphenyl-, tributyltetra-decyl-, trioctylmethyl-, benzyltrimethyl-, and benzyltriethylammonium fluoride and tetrabutyl-, tetraethyl-, tetraoctyl-, tetraphenyl-, tributyltetra-decyl-, trioctylmethyl-, benzyltrimethyl-, and benzyltriethylphosphonium fluoride, or else the corresponding quaternary ammonium or phosphonium hydrogen polyfluorides. Some of the latter are available commercially, or they can be obtained simply and in any desired stoichiometry by blending ammonium or phosphonium fluorides with HF. The HF may be employed in pure form or else as a solution in organic solvents. Alternatively, commercially available HF-amine complexes provide a suitable HF source. Furthermore, hydrogen polyfluorides can be obtained by ion exchange in the presence of potassium hydrogen fluoride (see D. Landini, H. Molinari, M. Penso, A. Rampoldi, Synthesis 1998, 953–955). Some of the simple quaternary ammonium and phosphonium fluorides are available commercially. In other cases, they can easily be obtained by halogen substitution from the parent halides (see S. Dermeik, Y. Sasson, J. Org. Chem. 1989, 54, 4827–4829, incorporated herein by reference).

The catalysts and compounds of the invention can be prepared in situ, i.e. the catalyst is generated in the isocyanate matrix whose trimerization is to be carried out. For this purpose, the components needed to form the catalyst are admixed independently of one another to the corresponding isocyanate. Alternatively, the catalyst components can first be reacted with one another without solvent or in a solvent, and the catalyst prefabricated in this way.

The invention further provides for the use of the catalysts and compounds of the invention for trimerizing mono-, di- or polyisocyanates.

The invention provides, furthermore, a process for preparing polyisocyanates containing isocyanurate groups by catalytically induced trimerization of organic mono-, di- or polyisocyanates, the trimerization catalysts employed being catalysts of the general formula (I) according to the invention.

The invention further provides the polyisocyanates prepared by the process of the invention.

In order to prepare the polyisocyanates it is possible to use any known aliphatic, cycloaliphatic, araliphatic, and aromatic mono-, di-, and polyisocyanates with an NCO content of less than 70 percent by weight in pure form or as any desired mixtures with one another. Examples that may be listed include the following: cyclohexane diisocyanates, methylcyclohexane diisocyanates, ethylcyclohexane diisocyanates, propylcyclohexane diisocyanates, methyldiethylcyclohexane diisocyanates, phenylene diisocyanates, tolylene diisocyanates, bis(isocyanato-phenyl)methane, propane diisocyanates, butane diisocyanates, pentane diisocyanates, hexane diisocyanates (e.g., hexamethylene diisocyanate (HDI) or 1,5-diisocyanato-2-methylpentane (MPDI)), heptane diisocyanates, octane diisocyanates, nonane diisocyanates (e.g., 1,6-diisocyanato-2,4,4-trimethyl-hexane and 1,6-diisocyanato-2,2,4-trimethylhexane (TMDI)), nonane triisocyanates (e.g., 4-isocyanato-methyl-1,8-octane diisocyanate (TIN)), decane di- and triisocyanates, undecane di- and triisocyanates, dodecane di- and triisocyanates, isophorone diisocyanate (IPDI), bis(isocyanatomethylcyclohexyl)-methane ($H_{12}$MDI), isocyanatomethyl methylcyclohexyl isocyanates, 2,5(2,6)-bis(isocyanatomethyl)bicyclo-[2.2.1] heptane (NBDI), 1,3-bis(isocyanatomethyl)cyclo-hexane (1,3-$H_6$-XDI), and 1,4-bis(isocyanatomethyl)-cyclohexane (1,4-$H_6$-XDI). This list includes all of the regioisomers and stereoisomers of the isocyanates exemplified. Preference is given to using HDI, IPDI, MPDI, TMDI, 1,3- and 1,4-$H_6$-XDI, NBDI, and mixtures of HDI and IPDI.

Monoisocyanates as well can be converted into isocyanurates in the presence of the catalysts of the invention; examples of monoisocyanates include ethyl isocyanate, cyclohexyl isocyanate, phenyl isocyanate, tolyl isocyanate, benzyl isocyanate, and all regioisomers and stereoisomers of the following compounds: propyl isocyanates, hexyl isocyanates, octyl isocyanates, and methoxypropyl isocyanate.

In the process of the invention, the synthesis route by which the isocyanate used has been prepared, i.e., with or without the use of phosgene, is unimportant. It should be noted, however, that the amount of catalyst needed to achieve a desired NCO content depends, among other things, on the quality of the mono-, di- or polyisocyanate. From experience, an increasing amount of hydrolyzable chlorine compounds in the isocyanate necessitates an increase in the amount of catalyst, and so an inhibitory effect of the hydrolyzable chlorine on the catalyst can be assumed.

Like aminosilyl compounds, various fluoride donors, including ammonium and phosphonium fluorides, may also induce the trimerization of isocyanates (see Y. Nambu, T. Endo, J. Org. Chem. 1993, 58, 1932–1934; EP 896 009). The catalysts of the invention originating from reaction between these two species, however, have a higher trimerization activity. They may be deactivated chemically or, where appropriate, thermally.

For the preparation of the polyisocyanates containing isocyanurate groups it is unimportant whether the catalyst of the invention is soluble in the mono-, di- or polyisocyanate to be trimerized or not. Also, the hydrogen fluoride needed to form the hydrogen fluorides may be added in pure or dissolved form to the isocyanate (mixture) to be trimerized, before or during the trimerization. The same applies to substances which occur as HF donors under the reaction conditions.

The preparation of the polyisocyanates containing isocyanurate groups by partial trimerization may be conducted continuously (tube reactor or stirred vessel cascade) or else batchwise. The catalysts of the formula (I) according to the invention are used at low concentrations of between 0.01 and 5.0% by weight. The exact amount is dependent on the individual catalyst, on the target conversion, and on the process regime.

The trimerization may be conducted isothermally within a temperature range between 0° C. and 100° C., preferably between 20° C. and 80° C. The reaction may take place with quantitative reaction of the participating isocyanate groups of the starting (poly)isocyanate/mixture or may be interrupted at any desired degree of conversion. It is preferred to aim for a conversion of 10–50%. Once the desired conversion has been achieved, the trimerization is stopped by adding (sub)stoichiometric amounts of a deactivator. Compounds suitable for inhibiting the catalyst system include, for example, acids or acid derivatives such as HCl, organic sulfonic acids, or acidic esters of phosphorous acid and phosphoric acid.

The reaction regime may also be designed exothermally. In this case, the temperature of the reaction mixture composed of the catalyst of the invention and the starting (poly)isocyanate or the starting (poly)isocyanate mixture is heated to 120–160° C., preferably to 80–120° C., for the purpose of initiating the exothermic trimerization. Alternatively, the ingredients needed to form the catalyst of the invention, or the catalyst in prefabricated form, may also be metered in after the starting (poly)isocyanate or the starting (poly)isocyanate mixture has reached the temperature necessary for initiation of the exothermic reaction. The exact temperature at which the exothermic reaction is initiated is a function, among other things, of the isocyanate, of the individual catalyst, and of the catalyst concentration, and can easily be determined experimentally. As a general rule, the catalyst of the invention is thermally destroyed in the course of the exothermic trimerization, during which temperatures of up to 220° C. prevail.

The process of the invention can be conducted either solventlessly or with dilution of the mono-, di- or polyisocyanates or mixtures thereof to be trimerized. Compounds suitable for effecting dilution include in principle all organic compounds which are inert toward NCO groups, such as toluene, xylene(s), higher aromatics, ethers, and esters, for example. The solvent-free variant is preferred.

For preparing polyisocyanates containing isocyanurate groups, the catalysts of the formula (I) according to the invention are used preferably in amounts of 0.01–5% by weight, more preferably 0.02–3% by weight, based on the weight of the starting (poly)isocyanate or starting (poly) isocyanate mixture(s) employed. The exact amount can easily be determined experimentally and is dependent on the catalytic activity of the individual catalyst, on the target conversion, and on the process-regime. The trimerization may be conducted isothermally or exothermally, continuously or batchwise. Following chemical or thermal deactivation of the catalyst, the unreacted monomer, whether it be monoisocyanate, diisocyanate or low molecular mass polyisocyanate, can be separated off by short-path evaporation, thin-film evaporation or extraction and then used again. The removal of excess starting isocyanate(s) is preferable if the process products of the invention are intended for applications in the polyurethane coatings sector.

The invention also provides for the use of the isocyanurate-functional polyisocyanates, free from monomer, as intermediates for polyurethane coatings, for polyurethane dispersions, adhesives, and as a polyisocyanate component in 1- and 2-component polyurethane systems.

The monomer-free isocyanurate-functional polyisocyanates prepared in accordance with the invention constitute useful intermediates for polyurethane coatings, i.e., leather coatings and textile coatings, and for polyurethane dispersions and adhesives, and are particularly valuable as polyisocyanate components in 1- and 2-component polyurethane systems for weather-stable and light-stable polyurethane coating materials. The process products of the invention may be used either as they are or else in a form in which they have been blocked with blocking agents. Examples of suitable blocking agents include lactams such as $\epsilon$-caprolactam, oximes such as methyl ethyl ketoxime or butanone oxime, triazoles such as 1H-1,2,4-triazole, readily enolizable compounds such as acetoacetates or acetylacetone, or else malonic acid derivatives, such as malonic diesters having 1–10 carbon atoms in the alcohol residues.

EXAMPLES

Having generally described this invention, a further understanding can be obtained by reference to certain specific examples which are provided herein for purposes of illustration only and are not intended to be limiting unless otherwise specified. Unless indicated otherwise, all percentages are by weight. All of the reactions were carried out under a nitrogen atmosphere.

Example 1

Preparation of the Catalyst 20 g (0.11 mol) of heptamethyldisilazane were admixed dropwise at room temperature with 11 ml of a 1-molar solution of tetrabutylammonium fluoride in THF. The reaction mixture was shaken vigorously for 2 hours in an automatic shaker. After the shaking process was stopped, two clear phases formed. The lower phase, containing the catalyst of the invention, was separated off and used for the HDI trimerization experiment described below (Example 2).

Example 2

Trimerization in the Presence of the Prefabricated Catalyst 400 g of HDI were admixed dropwise at room temperature with 2 ml of the inventive catalyst solution from Example 1, with stirring. Owing to very high local concentrations of the highly reactive catalyst at the point of dropwise addition, a small amount of clumping of the HDI was observed at that point. After all of the catalyst had been added, the temperature of the reaction solution was raised to about 100° C. After the exothermic trimerization reaction had been initiated, the heating source was removed. The temperature of the reaction mixture rose within 40 seconds to a maximum (about 210° C.) and fell back again following the thermal deactivation of the catalyst that occurred in the course of the reaction. The reaction mixture was cooled to room temperature and filtered through a folded filter and the excess monomer was separated from the polyisocyanate by short-path evaporation. The demonomerized resin had an NCO content of 20.2%.

Example 3

In Situ Preparation of the Catalyst and Trimerization a) A mixture of 800 g of HDI, 0.24 g (0.03%) of tetrabutylammonium fluoride and 0.14 g (0.018%) of heptamethyldisilazane was slowly heated with stirring until the initiation temperature of the exothermic trimerization was reached (about 120° C.). The heating source was removed and the temperature of the reaction mixture rose within 60 seconds to 232° C. The reaction mixture was cooled to room temperature and the excess monomer was separated from the polyisocyanate by short-path evaporation. The demonomerized resin had an NCO content of 20.7%.

b) A mixture of 800 g of HDI and 0.62 g (0.08%) of tetrabutylammonium fluoride and 1.4 g (0.18%) of heptamethyldisilazane was stirred at 50° C. for 20 minutes. The NCO content of the reaction mixture was 40.1% (about 36% conversion). The reaction was stopped by adding 5.8 g of a 2.5% strength solution of HCl in HDI, and excess monomer was separated off by short-path evaporation. The monomer-free polyisocyanate had an NCO content of 22.2%.

Example 4

In Situ Preparation of the Catalyst and Trimerization a) A mixture of 800 g of HDI and 0.64 g (0.08%) of tetrabutylammonium fluoride trihydrate and 1.4 g (0.18%) of heptamethyldisilazane was stirred at 60° C. for 40 minutes. The NCO content of the reaction mixture was 40.2% (about 36% conversion). The reaction was stopped by adding 2.5 g of a 2.9% strength solution of HCl in HDI, and excess monomer was separated off by short-path evaporation. The monomer-free polyisocyanate had an NCO content of 22.2%.

b) A mixture of 800 g of HDI and 0.71 g (0.09%) of tetraphenylphosphonium fluoride (ground in a mortar) and 1.4 g (0.18%) of heptamethyldisilazane was stirred at 50° C. for 15 minutes. The mixture was cooled to 30° C. and the reaction was stopped by adding 5.0 g of a 2.9% strength solution of HCl in HDI. The NCO content of the reaction mixture was 39.0% (about 39% conversion). Excess monomer was separated off by short-path evaporation. The monomer-free polyisocyanate had an NCO content of 22.0%.

c) A mixture of 800 g of HDI and 8 g (1.0%) of tetrabutylammonium fluoride on silica gel (1.0–1.5 mol fluoride per gram) and 1.4 g (0.18%) of heptamethyldisilazane was stirred at 50° C. for 90 minutes. The NCO content of the reaction mixture was 41.1% (about 32% conversion). The silica gel was removed from the reaction mixture by filtration and the filtrate was admixed with 5.8 g of a 2.5% strength solution of HCl in HDI. Excess monomer was separated off by short-path evaporation. The monomer-free polyisocyanate had an NCO content of 22.8%.

d) A mixture of 800 g of HDI and 16 g (1.0%) of tetrabutylammonium fluoride on alumina (about 15% by weight) and 1.4 g (0.18%) of heptamethyldisilazane was stirred at 70° C. for 70 minutes. The NCO content of the reaction mixture was 40.6% (about 34% conversion). The alumina was removed from the reaction mixture by filtration and the filtrate was admixed with 5.8 g of a 2.5% strength solution of HCl in HDI. Excess monomer was separated off by short-path evaporation. The monomer-free polyisocyanate had an NCO content of 22.3%.

e) A mixture of 800 g of HDI and 0.68 g (0.09%) of tetrabutylammonium hydrogen difluoride (50% strength in dichloromethane) and 1.4 g (0.18%) of heptamethyldisilazane was stirred at 50° C. for 180 minutes. The NCO content of the reaction mixture was 40.4% (about 36% conversion). The reaction was stopped by adding 3.5 g of a 2.9% strength solution of HCl in HDI and excess monomer was separated off by short-path evaporation. The monomer-free polyisocyanate had an NCO content of 22.6%.

f) A mixture of 800 g of HDI and 0.64 g (0.08%) of tetrabutylammonium fluoride and 1.5 g (0.19%) of diethylaminotrimethylsilane was stirred at 60° C. for 60 minutes. The NCO content of the reaction mixture was 39.9% (about 36% conversion). The reaction was stopped by adding 1.7 g of dibutyl phosphate and excess monomer was separated off by short-path evaporation. The monomer-free polyisocyanate had an NCO content of 22.1 %.

g) A mixture of 800 g of HDI and 0.63 g (0.08%) of tetrabutylammonium fluoride and 1.8 g (0.23%) of nonamethyltrisilazane was stirred at 80° C. for 45 minutes. The NCO content of the reaction mixture was 39.5% (about 38% conversion). The reaction was stopped by adding 1.7 g of dibutyl phosphate and excess monomer was separated off by short-path evaporation. The monomer-free polyisocyanate had an NCO content of 22.1 %.

Example 5

In Situ Preparation of the Catalyst and Trimerization a) A mixture of 800 g of IPDI and 1.0 g (0.125%) of tetrabutylammonium fluoride and 1.0 g (0.125%) of heptamethyldisilazane was stirred at 70° C. for 15 minutes. The NCO content of the reaction mixture was 30.3% (about 40% conversion). The reaction was stopped by adding 8.3 g of a 2.5% strength solution of HCl in HDI, the reaction mixture was filtered, and excess monomer was separated off by short-path evaporation. The monomer-free polyisocyanate had an NCO content of 17.8%.

b) A mixture of 800 g of IPDI and 1.15 g (0.14%) of tetraphenylphosphonium fluoride (ground in a mortar) and 1.12 g (0.14%) of heptamethyldisilazane was stirred at 70° C. for 2.5 hours. The NCO content of the reaction mixture was 34.0% (about 20% conversion). The reaction was stopped by adding 0.67 g of dibutyl phosphate, the reaction mixture was filtered, and excess monomer was separated off by short-path evaporation. The monomer-free polyisocyanate had an NCO content of 17.8%.

Example 6

Comparative Example, not Inventive a) A mixture of 1000 g of HDI and 10 g (1%) of heptamethyldisilazane was stirred at 140° C. for 2 hours. The reaction mixture was then cooled to room temperature and its NCO content was found to be 38.6% (corresponding to a conversion of about 40%). Following deactivation of the catalyst with 4 g of methanol, excess HDI was removed by short-path evaporation. The monomer-free polyisocyanate had an NCO content of 21.8%.

b) A mixture of 800 g of HDI and 4 g (0.5%) of heptamethyldisilazane was stirred at 140° C. for 4 hours. The reaction mixture was then cooled to room temperature and its NCO content was found to be 40.1% (corresponding to a conversion of about 36%). Following deactivation of the catalyst with 1.6 g of methanol, excess HDI was removed by short-path evaporation. The monomer-free polyisocyanate had an NCO content of 22.0%.

c) A mixture of 800 g of HDI and 8 g (1%) of heptamethyldisilazane was stirred at 100° C. for 8 hours. The reaction mixture was then cooled to room temperature and its NCO content was found to be 39.9% (corresponding to a conversion of about 36%). Following deactivation of the catalyst with 3.2 g of methanol, excess HDI was removed by short-path evaporation. The monomer-free polyisocyanate had an NCO content of 21.9%.

Example 7

Comparative Example, not Inventive

A mixture of 800 g of IPDI and 8 g (1%) of heptamethyldisilazane was stirred at 100° C. for 2 hours. After no conversion was found, it was left stirring at 140° C. for a further 2 hours. The conversion was less than 3%. The reaction was terminated, and in view of the low conversion the reaction mixture was not worked up.

Example 8

Comparative Example, not Inventive a) A mixture of 800 g of HDI and 0.24 g (0.03%) of tetrabutylammonium fluoride was heated to 100° C. and left at this temperature for 20 minutes. When no conversion could be ascertained, the temperature was raised further and the reaction mixture was stirred at 140° C. for 20 minutes. The conversion was less than 1%. The reaction was terminated, and in view of the low conversion the reaction mixture was not worked up.

b) A mixture of 800 g of HDI and 0.62 g (0.08%) of tetrabutylammonium fluoride was stirred at 60° C. for 1 hour. The NCO content of the reaction mixture was 39.9% (about 36% conversion). The reaction was terminated by adding 1.72 g of a 2.5% strength solution of HCl in HDI, and excess monomer was separated off by short-path evaporation. The monomer-free polyisocyanate had an NCO content of 22.2%.

Example 9

Comparative Example, not Inventive

A mixture of 800 g of IPDI and 4.0 g (0.5%) of tetrabutylammonium fluoride was stirred at 70° C. for 15 minutes. The NCO content of the reaction mixture was 31.7% (about 32% conversion). The reaction was terminated by adding 22.4 g of a 2.5% strength solution of HCl in HDI, the reaction mixture was filtered, and excess monomer was separated off by short-path evaporation. The monomer-free polyisocyanate had an NCO content of 17.6%.

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 0160305.3, filed on Dec. 7, 2001, and incorporated herein by reference.

What is claimed is:

1. A catalyst suitable for the trimerization of isocyanates represented by the formula (I):

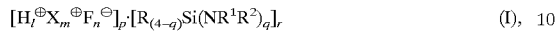 (I), wherein n=m+l with $1 \geq m/n > 0$, and $l \geq 0$, p>0 and r>0, and the ratio p/r is any value, q=1 or 2, R simultaneously or independently of one another represents a saturated or unsaturated, linear or branched aliphatic or cycloaliphatic radical or aryl, aralkyl, or alkylaryl radical having from 1 to 16 carbon atoms, wherein two radicals R are optionally linked to one another via an alkylene bridge, $R^1$ represents R, $SiR_3$ or an amide radical represented by the formula (II):

 (II), $R^2$ is R or H, wherein $R^2$, when $R^1$ is not an amide radical, is optionally linked to $R^1$ via an alkylene bridge, $R^3$ is R or $SiR_3$, and $X^\oplus$ represents an organic onium cation represented by the formula (III):

 (III), where

E is nitrogen or phosphorus, and $R^4$ represents identical or different, linear or branched aliphatic, cycloaliphatic or araliphatic radicals having from 1 to 20 carbon atoms.

2. The catalyst of claim 1, wherein $1 \geq m/n \geq 0.1$.

3. The catalyst of claim 1, wherein $1 \geq m/n \geq 0.25$.

4. The catalyst of claim 1, wherein the ratio p/r is between 0.01 and 100.

5. The catalyst of claim 1, wherein the ratio p/r is between 0.1 and 10.

6. The catalyst of claim 1, wherein R simultaneously or independently of one another represents a saturated or unsaturated, linear or branched aliphatic or cycloaliphatic radical having from 1 to 16 carbon atoms, wherein two radicals R are optionally linked to one another via an alkylene bridge.

7. The catalyst of claim 1, wherein R simultaneously or independently of one another represents an aryl, aralkyl, or alkylaryl radical having from 1 to 16 carbon atoms, wherein two radicals R are optionally linked to one another via an alkylene bridge.

8. The catalyst of claim 1, wherein the organosilicon moiety of formula (I) is methylaminotrimethylsilane, dimethylaminotrimethylsilane, dibutylaminotrimethylsilane, diethylaminodimethylphenylsilane, bis(dimethylamino)dimethylsilane, bis(diethyl-amino)dimethylsilane, bis(dibutylamino)dimethyl-silane, bis(dimethylamino)methylphenylsilane, N-methyl-N-trimethylsilyl-N'-methyl-N'-butylurea, N-trimethylsilyl-N-methyl-N', N'-dimethylurea, N-trimethylsilyl-N-ethyl-N',N'-dimethylurea, N-trimethylsilyl-N-butyl-N'-butyl-N'-trimethylsilylurea, trimethylsilylpyrrolidine, trimethylsilylmorpholine, trimethylsilyl-piperidine, trimethylsilylpiperazine, hexamethyldisilazane, heptamethyldisilazane, 1,3-diethyl-1,1,3,3-tetramethyldisilazane, hexaethyldisilazane, or 1,3-diphenyl-1,1,3,3-tetramethyldisilazane.

9. The catalyst of claim 1, wherein q is 1.

10. The catalyst of claim 1, wherein q is 2.

11. The catalyst of claim 1, wherein E is nitrogen.

12. The catalyst of claim 1, wherein E is phosphorous.

13. A catalyst suitable for the trimerization of isocyanates obtained by reacting a fluoride compound represented by the formula:

with an organosilicon compound represented by the formula:

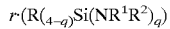

wherein n=m+l with $1 \geq m/n > 0$, and $l \geq 0$, p>0 and r>0, and the ratio p/r is any value, q=1 or 2, R simultaneously or independently of one another represents a saturated or unsaturated, linear or branched aliphatic or cycloaliphatic radical or aryl, aralkyl, or alkylaryl radical having from 1 to 16 carbon atoms, wherein two radicals R are optionally linked to one another via an alkylene bridge, $R^1$ represents R, $SiR_3$ or an amide radical represented by the formula (II):

 (II), $R^2$ is R or H, wherein $R^2$, when $R^1$ is not an amide radical, is optionally linked to $R^1$ via an alkylene bridge, $R^3$ is R or $SiR_3$, and $X^\oplus$ represents an organic onium cation represented by the formula (III):

 (III), where

E is nitrogen or phosphorus, and $R^4$ represents identical or different, linear or branched aliphatic, cycloaliphatic or araliphatic radicals having from 1 to 20 carbon atoms.

14. The catalyst of claim 13, wherein $1 \geq m/n \geq 0.1$.

15. The catalyst of claim 13, wherein $1 \geq m/n \geq 0.25$.

16. The catalyst of claim 13, wherein the ratio p/r is between 0.01 and 100.

17. The catalyst of claim 13, wherein the ratio p/r is between 0.1 and 10.

18. The catalyst of claim 13, wherein the organosilicon compound is an amino silane, silyl urea, or silazane.

19. A catalyst of claim 13, wherein the organosilicon compound is methylaminotrimethylsilane, dimethylaminotrimethylsilane, dibutylaminotrimethylsilane, diethylaminodimethylphenylsilane, bis(dimethylamino)dimethylsilane, bis(diethyl-amino)dimethylsilane, bis(dibutylamino)dimethyl-silane, bis (dimethylamino)methylphenylsilane, N-methyl-N-trimethylsilyl-N'-methyl-N'-butylurea, N-trimethylsilyl-N-methyl-N',N'-dimethylurea, N-trimethylsilyl-N-ethyl-N',N'-dimethylurea, N-trimethylsilyl-N-butyl-N'-butyl-N'-trimethylsilylurea, trimethylsilylpyrrolidine, trimethylsilylmorpholine, trimethylsilyl-piperidine, trimethylsilylpiperazine, hexamethyldisilazane, heptamethyldisilazane, 1,3-diethyl-1,1,3,3-tetramethyldisilazane, hexaethyldisilazane, or 1,3-diphenyl-1,1,3,3-tetramethyldisilazane.

20. The catalyst of claim 13, wherein the fluoride compound is selected from the group consisting of quaternary ammonium fluorides, quarternary phosphonium fluorides, quaternary ammonium hydrogen polyfluorides, and quarternary phosphonium hydrogen polyfluorides.

21. The catalyst of claim 13, wherein the fluoride compound is selected from the group consisting of tetrabutyl-, tetraethyl-, tetraoctyl-, tetraphenyl-, tributyltetradecyl-, trioctylmethyl-, benzyltrimethyl-, and benzyltriethyl-ammonium fluoride, tetrabutyl-, tetraethyl-, tetraoctyl-, tetraphenyl-, tributyltetradecyl-, trioctylmethyl-, benzyltrimethyl-, and benzyltriethyl-phosphonium fluoride, and the corresponding quaternary ammonium hydrogen polyfluorides, and quaternary phosphonium hydrogen polyfluorides.

22. The catalyst of claim 13, wherein q is 1.
23. The catalyst of claim 13, wherein q is 2.
24. The catalyst of claim 13, wherein E is nitrogen.
25. The catalyst of claim 13, wherein E is phosphorous.
26. The catalyst of claim 13, wherein R simultaneously or independently of one another represents a saturated or unsaturated, linear or branched aliphatic or cycloaliphatic radical having from 1 to 16 carbon atoms, wherein two radicals R are optionally linked to one another via an alkylene bridge.
27. The catalyst of claim 13, wherein R simultaneously or independently of one another represents an aryl, aralkyl, or alkylaryl radical having from 1 to 16 carbon atoms, wherein two radicals R are optionally linked to one another via an alkylene bridge.
28. A process for preparing the catalyst of claim 1, comprising:

reacting a fluoride compound represented by the formula:

with an organosilicon compound represented by the formula:

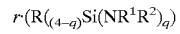

wherein $n=m+l$ with $1 \geq m/n > 0$, and $l \geq 0$, $p>0$ and $r>0$, and the ratio $p/r$ is any value, $q=1$ or 2, R simultaneously or independently of one another represents a saturated or unsaturated, linear or branched aliphatic or cycloaliphatic radical or aryl, aralkyl, or alkylaryl radical having from 1 to 16 carbon atoms, wherein two radicals R are optionally linked to one another via an alkylene bridge, $R^1$ represents R, $SiR_3$ or an amide radical represented by the formula (II):

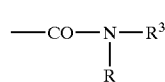

(II), $R^2$ is R or H, wherein $R^2$, when $R^1$ is not an amide radical, is optionally linked to $R^1$ via an alkylene bridge, $R^3$ is R or $SiR_3$, and $X^\oplus$ represents an organic onium cation represented by the formula (III):

(III), where

E is nitrogen or phosphorus, and $R^4$ represents identical or different, linear or branched aliphatic, cycloaliphatic or araliphatic radicals having from 1 to 20 carbon atoms.

29. A method of trimerizing mono-, di- or polyisocyanates, or any mixture thereof, comprising reacting a mono-, di- or polyisocyanate, or any mixture thereof in the presence of a catalyst represented by the formula (I):

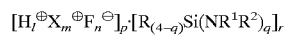

(I), wherein $n=m+l$ with $1 \geq m/n > 0$, and $l \geq 0$, $p>0$ and $r>0$, and the ratio $p/r$ is any value, $q=1$ or 2, and R simultaneously or independently of one another represents a saturated or unsaturated, linear or branched aliphatic or cycloaliphatic radical or aryl, aralkyl, or alkylaryl radical having from 1 to 16 carbon atoms, wherein two radicals R are optionally linked to one another via an alkylene bridge, $R^1$ represents R, $SiR_3$ or an amide radical represented by the formula (II):

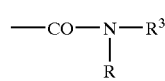

(II), $R^2$ is R or H, wherein $R^2$, when $R^1$ is not an amide radical, is optionally linked to $R^1$ via an alkylene bridge, $R^3$ is R or $SiR_3$, and $X^\oplus$ represents an organic onium cation represented by the formula (III):

(III), where

E is nitrogen or phosphorus, and $R^4$ represents identical or different, linear or branched aliphatic, cycloaliphatic or araliphatic radicals having from 1 to 20 carbon atoms.

30. The method of claim 29, wherein the mono-, di- or polyisocyanate is selected from the group consisting of cyclohexane diisocyanates, methylcyclohexane diisocyanates, ethylcyclohexane diisocyanates, propylcyclohexane diisocyanates, methyldiethyl-cyclohexane diisocyanates, phenylene diisocyanates, tolylene diisocyanates, bis(isocyanatophenyl)methane, propane diisocyanates, butane diisocyanates, pentane diisocyanates, hexane diisocyanates, heptane diisocyanates, octane diisocyanates, nonane diisocyanates, nonane triisocyanates, decane di- and triisocyanates, undecane di- and triisocyanates, dodecane di- and triisocyanates, isophorone diisocyanate (IPDI), bis(isocyanatomethylcyclo-hexyl) methane ($H_{12}$MDI), isocyanatomethyl methylcyclohexyl isocyanates, 2,5(2,6)-bis(iso-cyanatomethyl)bicyclo[2.2.1] heptane (NBDI), 1,3-bis(isocyanatomethyl)cyclohexane (1,3-$H_6$-XDI), and 1,4-bis(isocyanatomethyl)cyclohexane (1,4-$H_6$-XDI).

31. The method of claim 29, wherein the mono-, di- or polyisocyanate is selected from the group consisting of HDI, IPDI, MPDI, TMDI, 1,3- and 1,4-$H_6$-XDI, NBDI, and mixtures of HDI and IPDI.

32. The method of claim 29, wherein the mono-, di- or polyisocyanate is selected from the group consisting of ethyl isocyanate, cyclohexyl isocyanate, phenyl isocyanate, tolyl isocyanate, benzyl isocyanate, and all regioisomers and stereoisomers of the following compounds: propyl isocyanates, hexyl isocyanates, octyl isocyanates, and methoxypropyl isocyanate.

33. The method of claim 32, which is conducted continuously or batchwise.

34. The method of claim 29, wherein the catalyst is used at a concentration of from 0.01 to 5.0% by weight.

35. The method of claim 29, which is conducted at temperature from 0° C. to 100° C.

36. The method of claim 29, which is conducted at temperature from 20° C. and 80° C.

37. A process for preparing a polyisocyanate containing isocyanurate groups, comprising trimerizing an organic mono-, di- or polyisocyanate in the presence of the catalyst of claim 1.

38. The process of claim 37, wherein the mono-, di- or polyisocyanate is an aliphatic, cycloaliphatic, araliphatic, or aromatic.

39. The method of claim 37, wherein the mono-, di- or polyisocyanate is selected from the group consisting of cyclohexane diisocyanates, methylcyclohexane diisocyanates, ethylcyclohexane diisocyanates, propylcyclohexane diisocyanates, methyldiethyl-cyclohexane diisocyanates, phenylene diisocyanates, tolylene diisocyanates, bis(isocyanatophenyl)methane, propane diisocyanates, butane diisocyanates, pentane diisocyanates, hexane diisocyanates, heptane diisocyanates, octane diisocyanates, nonane diisocyanates, nonane triisocyanates, decane di- and triisocyanates, undecane di- and triisocyanates, dodecane di- and triisocyanates, isophorone diisocyanate (IPDI), bis(isocyanatomethylcyclo-hexyl) methane ($H_{12}$MDI), isocyanatomethyl methylcyclohexyl isocyanates, 2,5(2,6)-bis(iso-cyanatomethyl)bicyclo[2.2.1] heptane (NBDI), 1,3-bis(isocyanatomethyl)cyclohexane (1,3-$H_6$-XDI), and 1,4-bis(isocyanatomethyl)cyclohexane (1,4-$H_6$-XDI).

40. The method of claim 39, wherein the mono-, di- or polyisocyanate is selected from the group consisting of HDI, IPDI, MPDI, TMDI, 1,3- and 1,4-$H_6$-XDI, NBDI, and mixtures of HDI and IPDI.

41. The method of claim 39, wherein the mono-, di- or polyisocyanate is selected from the group consisting of ethyl isocyanate, cyclohexyl isocyanate, phenyl isocyanate, tolyl isocyanate, benzyl isocyanate, and all regioisomers and stereoisomers of the following compounds: propyl isocyanates, hexyl isocyanates, octyl isocyanates, and methoxypropyl isocyanate.

42. The method of claim 39, which is conducted continuously or batchwise.

43. The method of claim 39, wherein the catalyst is used at a concentration of from 0.01 to 5.0% by weight.

44. The method of claim 39, which is conducted at temperature from 0° C. to 100° C.

45. The method of claim 39, which is conducted at temperature from 20° C. and 80° C.

46. A polyisocyanate containing isocyanurate groups, obtained from the process of claim 37.

47. A polyurethane coating, polyurethane dispersion, adhesive, 1-component polyurethane system, or 2-component polyurethane system, obtained from the polyisocyanate of claim 46.

48. A leather or textile article coated with the polyurethane coating of claim 47.

* * * * *